United States Patent

Miraki et al.

Patent Number: 5,383,890
Date of Patent: Jan. 24, 1995

[54] LOW-PROFILE SINGLE-LUMEN PERFUSION BALLOON CATHETER

[75] Inventors: Manouchehr Miraki, Aliso Viejo; Blair Walker, Long Beach; Sheryl W. Higgins, Silverado, all of Calif.

[73] Assignee: Baxter International Inc., Deerfield, Ill.

[21] Appl. No.: 143,946

[22] Filed: Oct. 27, 1993

[51] Int. Cl.⁶ ............................................. A61M 29/00
[52] U.S. Cl. ....................................... 606/194; 604/96
[58] Field of Search ....................... 606/191, 192, 194; 604/95–101, 282

[56] References Cited

U.S. PATENT DOCUMENTS

| | | |
|---|---|---|
| 3,811,448 | 5/1974 | Morton . |
| 4,681,564 | 7/1987 | Landreneau . |
| 4,944,745 | 7/1990 | Sogard et al. ............... 606/194 |
| 5,000,734 | 3/1991 | Boussignac . |
| 5,078,685 | 1/1992 | Colliver .................... 606/194 |
| 5,092,873 | 3/1992 | Simpson . |
| 5,112,303 | 5/1992 | Pudenz . |
| 5,146,916 | 9/1992 | Catalani . |
| 5,180,367 | 1/1993 | Kontos . |
| 5,195,971 | 3/1993 | Sirhan . |
| 5,217,482 | 6/1993 | Keith . |
| 5,279,562 | 1/1994 | Sirhan et al. ............... 604/96 |

FOREIGN PATENT DOCUMENTS

| | | |
|---|---|---|
| 52841 | 6/1982 | European Pat. Off. . |
| 212159 | 9/1988 | European Pat. Off. . |
| 0283122 | 9/1988 | European Pat. Off. . |
| 346012 | 12/1989 | European Pat. Off. . |
| 0370785 | 5/1990 | European Pat. Off. . |
| 0406901 | 1/1991 | European Pat. Off. . |
| 0435518 | 7/1991 | European Pat. Off. . |
| 0540783 | 5/1993 | European Pat. Off. . |
| 0546646 | 6/1993 | European Pat. Off. . |
| 521595A2 | 7/1993 | European Pat. Off. . |
| 476004 | 7/1915 | France . |
| 321666 | 4/1921 | Germany . |
| 823320 | 12/1951 | Germany . |
| 867144 | 12/1952 | Germany . |
| 4113265 | 3/1992 | Germany . |
| 933307 | 1/1960 | United Kingdom . |
| 1033971 | 4/1963 | United Kingdom . |
| 1567122 | 5/1980 | United Kingdom . |
| 2053000 | 2/1981 | United Kingdom . |
| 2092007 | 8/1982 | United Kingdom . |
| 2140304 | 11/1984 | United Kingdom . |
| 2140305 | 11/1984 | United Kingdom . |
| 2182567 | 10/1989 | United Kingdom . |
| WO89/02290 | 3/1989 | WIPO . |
| WO92/21398 | 12/1992 | WIPO . |

Primary Examiner—Stephen C. Pellegrino
Assistant Examiner—William W. Lewis
Attorney, Agent, or Firm—Poms Smith Lande & Rose

[57] ABSTRACT

A low-profile single-lumen perfusion and fluid delivery balloon catheter for dilatation angioplasty procedures includes a small diameter single-lumen catheter shaft carrying a dilatation balloon adjacent to the distal end thereof. A perfusion conduit is also carried by the catheter shaft and traverses the dilatation balloon to provide perfusion blood flow past the balloon when the latter is inflated. The catheter may be used in mono-rail configuration to facilitate retracing of a subsequent catheter or other therapeutic device along the mono-rail guide wire back to the vascular site under treatment.

28 Claims, 2 Drawing Sheets

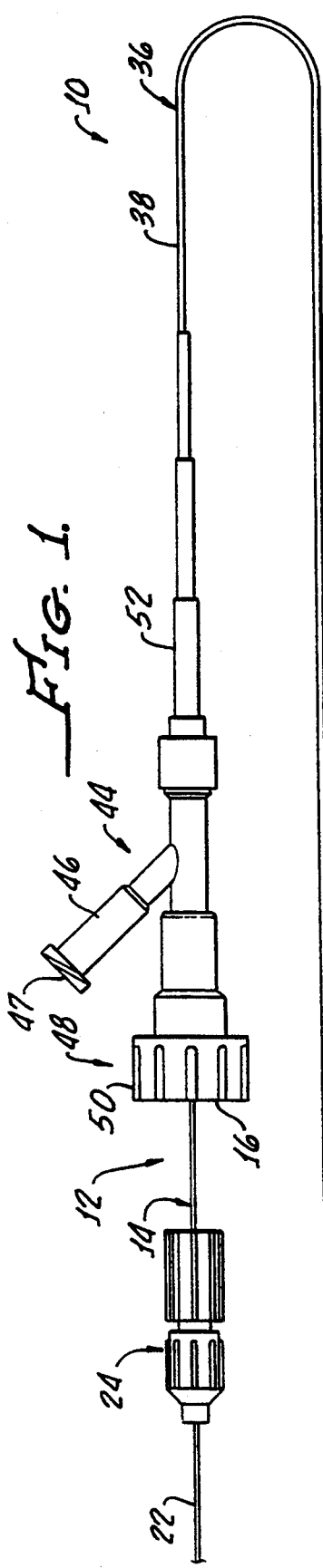
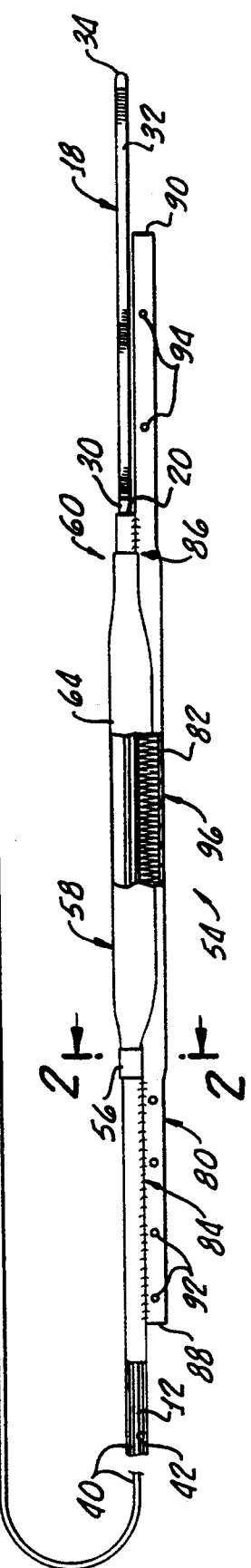
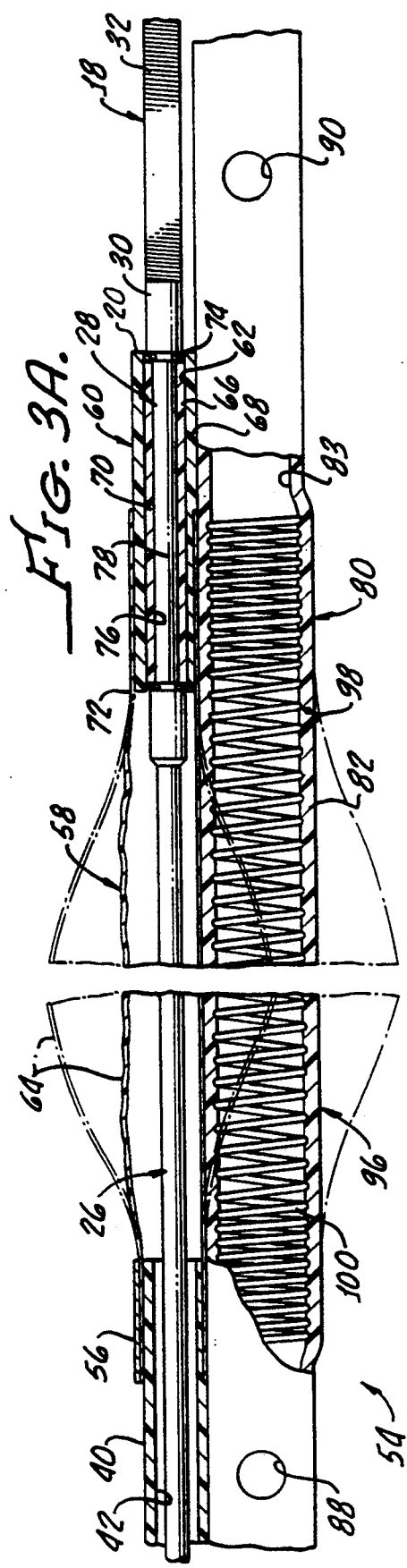

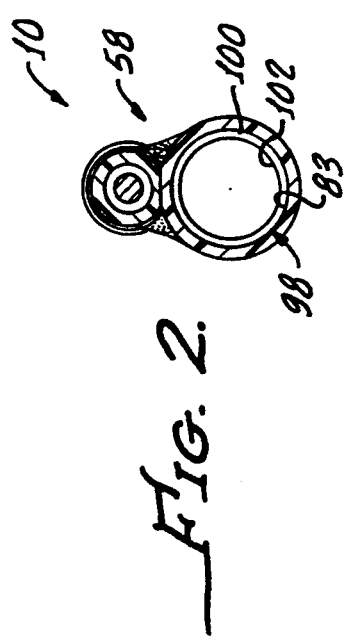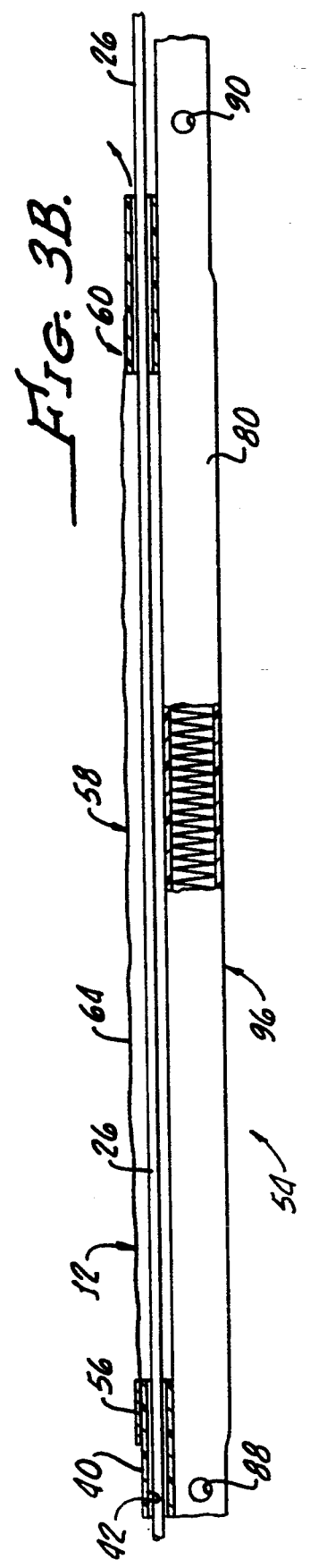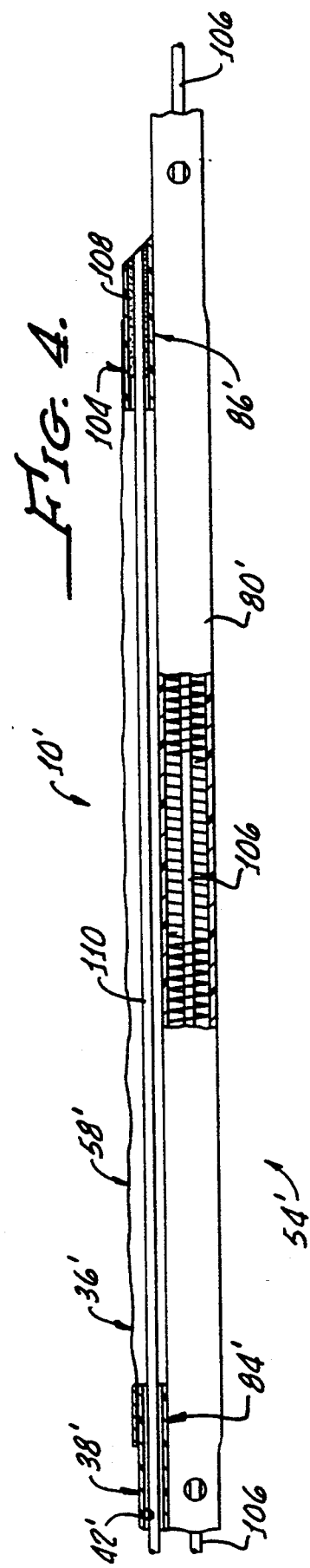

LOW-PROFILE SINGLE-LUMEN PERFUSION BALLOON CATHETER

BACKGROUND OF THE INVENTION

1. Field of the Invention

The present invention relates in general to the field of dilatation or balloon catheters employed in the treatment of vascular diseases. More particularly, the present invention relates to a low-profile single-lumen perfusion balloon catheter with an axially extending external perfusion conduit having a perfusion lumen traversing the dilatation balloon of the catheter. This perfusion conduit extends only a short distance along the length of the catheter and includes distal and proximal perfusion ports on opposite sides of the dilatation balloon communicating with one another via a lumen of the perfusion conduit. This perfusion conduit at the distal end portion of the catheter also facilitates mono-rail use of the catheter for catheter exchange purposes, if desired.

2. Related Technology

Over the past decade the medical procedure known as angioplasty has become widely accepted as a safe and effective method for treating various types of vascular diseases. For example, angioplasty is widely used for opening stenoses throughout the vascular system and particularly for opening stenoses in coronary arteries.

At present, the most common form of angioplasty is called percutaneous transluminal coronary angioplasty (PTCA). This procedure utilizes a dilatation catheter having an inflatable balloon at its distal end. By using a fluoroscope and radiopaque dyes and markers on the catheter for visualization the distal end of the dilatation catheter is guided into position through a guide catheter and across the stenosis. With the dilatation balloon in this position of alignment with the stenosis the balloon is inflated for a brief duration to open the artery and establish adequate blood flow.

Typically, inflation of the balloon is accomplished by supplying pressurized fluid from an inflation apparatus located outside the patient's body through an inflation lumen in the catheter which communicates with the balloon. Conversely, applying a negative pressure to the inflation lumen collapses the balloon to its minimum dimension for initial placement or for removal of the balloon catheter from within the blood vessel receiving treatment.

In the past years a number of balloon catheter designs have been developed which have contributed to the safety and acceptability of PTCA and similar medical procedures. The most common design is known as an "over-the-wire" balloon catheter. This conventional device typically utilizes a relatively large lumen for passage of a guide wire and injection of contrast fluid (or angiographic visualization dye) to assist in the placement of the device. A second parallel lumen is provided for inflation and deflation of the balloon.

Typically, a steerable guide wire is positioned within the larger lumen and the entire assembly is maneuvered into an initial position within the target artery through a guide catheter which has been positioned previously, and which is of sufficient diameter to pass the angioplasty catheter. Once near the site of the stenoses the guide wire can be rotated and axially extended or retracted into position across the lesion. The therapeutic angioplasty catheter is subsequently advanced along the guide wire to position its balloon end portion across the lesion prior to inflation of the balloon and dilatation of the stenosis.

An alternative conventional over-the-wire catheter assembly utilizes a non-removable guide wire that allows for longitudinal or axial movement. However, this design has a significant drawback because the entire catheter assembly with its non-removable guide wire must be removed to accomplish replacement or exchange of the balloon. In some cases of PTCA it is necessary to replace the balloon with one of different diameter or configuration following the initial dilatation.

However, cases of acute re-closure have been noted where the lesion closes again following dilatation and removal of the balloon catheter. One response to this re-closure problem has been the placement of an expandable stent into the artery at the lesion with another replacement balloon catheter. This alternative system increases the difficulties of these subsequent procedures by requiring that the replacement catheter renegotiate the entire placement path without the advantage of a guide wire.

A "mono-rail" variant of the standard balloon-over-a-wire system also has been developed in which only the distal portion of the balloon catheter tracks over the guide wire. This system utilizes a conventional inflation lumen and a relatively short guiding or through lumen adjacent to the distal end of the catheter. Principal benefits of the monorail construction of therapeutic catheter are the reduction of frictional drag over the length of the externally located guide wire and the ease of balloon exchange. This construction provides the ability to recross an acutely closed vessel or to exchange balloons without removing the guide wire.

However, a disadvantage of this "mono-rail" design is the increased difficulty in steering the guide wire because the guide wire is not supported by the balloon catheter. Also, the balloon catheter itself may not be pushable to move along the guide wire. Some versions of the monorail use an external flexible pusher member which also tracks the guide wire and is used to move the therapeutic catheter to the desired location near the distal end of the guide wire. Additionally, the dual lumen distal design of the monorail catheters produces a larger profile and catheter shaft size.

Another innovation in dilatation catheter design which is now conventional is the "fixed-wire" or integrated "balloon-on-a-wire" dilatation catheter. These single lumen designs utilize a relatively narrow wire positioned within the inflation lumen and permanently fixed to the distal end of the balloon. This construction produces a low-profile catheter assembly which is able to cross severely narrowed lesions and to navigate tortuous vascular pathways. Additionally, the fixed guide wire bonded at the distal end of the balloon improves the steerability and pushability of these designs which enhances their maneuverability. The thin shaft design also improves coronary visualization and enables all but the tightest critical lesions to be crossed.

However, though able to provide relatively quick and simple balloon placement as well as providing access to lesions otherwise unsuitable for PTCA, fixed-wire balloon-on-a-wire systems sacrifice the ability to maintain guide wire position across the lesion when exchanging balloons or the safety advantage of being able to recross an acutely closed vessel without repositioning the entire assembly.

Yet another difficulty arises when the dilatation balloon is inflated to dilate the vessel under treatment. While this balloon is inflated blood cannot circulate in the vessel. This lack of blood circulation can lead to necrosis of tissues already stressed by the previously reduced level of blood flow. As a solution to this problem, catheters have been provided with perfusion ports proximal and distal to the balloon and communicating with one another via a lumen of the catheter which extends through the balloon.

A conventional catheter of the type discussed immediately above is known in accord with U.S. Pat. No. 4,581,017, issued 8 Apr. 1986 to H. Sahota. This catheter is believed to include an elongate tubular shaft defining a guide wire and perfusion lumen, and an inflation lumen. A dilatation balloon is carried on the tubular shaft near the distal end thereof, and communicates with the inflation lumen. In order to allow perfusion blood flow past the inflated balloon, the catheter shaft defines at least one proximal and at least one distal perfusion port opening outwardly from the guide wire and perfusion lumen on opposite sides of the balloon. When the balloon is inflated to dilate the lesion, perfusion blood may flow through the guide wire lumen past the balloon.

Another conventional catheter also of this type is depicted in U.S. Pat. No. 5,160,321, issued 3 Nov. 1992, to H. Sahota. The catheter depicted in the Sahota patent employs a separate inner lumen to outwardly bound an annular axially extending passage through which blood may flow past the inflated balloon via perfusion ports. Also, this separate inner lumen inwardly defines a passage through which extends the guide wire assembly for the catheter.

However, with catheters of the type illustrated by the Sahota patents, and others of this type, the distal portion of the catheter is obstructed by the guide wire, or by the guide wire and its lumen. Consequently, the cross sectional area of the catheter lumen which is available for blood perfusion past the inflated balloon is very limited. While the distal end portion of the catheter may be made of a size sufficient to pass an adequate volume of blood, this size increase is contrary to the recognized advantages of having a low-profile catheter.

SUMMARY OF THE INVENTION

Accordingly, in view of the recognized deficiencies of conventional catheters discussed above, it is an object of the present invention to provide a low-profile, single-lumen, balloon perfusion catheter which during inflation of the balloon provides for circulation of patient blood through a perfusion conduit traversing the balloon.

An additional object for the present invention is to provide such a catheter with an internal guide wire lumen into which a guide wire may be received for guiding the catheter into a desired vascular pathway.

Yet another object for the present invention is provide such a catheter with a valving structure cooperatively defined by the guide wire and catheter shaft which allows a single lumen of the catheter to be utilized as a guide wire lumen, as an inflation lumen for the dilatation balloon, and as a fluid delivery lumen through which therapeutic or other material, such as visualization fluid, may be delivered to the site of a vascular lesion.

Yet another object for the present invention is to provide a catheter of the above-described type in which the external perfusion conduit is configured to facilitate optional use of this conduit as a mono-rail guide feature of the distal end portion of the catheter shaft.

Still another object of the present invention is to provide such a catheter with a flexible yet flexibly-supported perfusion conduit which allows the catheter distal end portion to be easily maneuverable in the vascular pathways which the catheter must negotiate, yet which prevents the inflation pressure of the dilatation balloon from collapsing the perfusion conduit.

Other features and advantages of the present invention will become apparent from the following detailed description of exemplary and preferred embodiments of the invention, taken in conjunction with the accompanying drawings which illustrate, by way of example, the principals of the present invention.

BRIEF DESCRIPTION OF THE DRAWINGS

FIG. 1 presents a fragmentary view in plan of a single-lumen, low-profile, perfusion balloon catheter, with portions of the view shown at different scales to better depict salient features of the invention;

FIG. 2 is an enlarged cross-sectional view taken at line 2—2 of FIG. 1;

FIG. 3A is a partial longitudinal cross sectional view of the distal portion of the low-profile, single-lumen perfusion balloon catheter of FIG. 1 shown at a more enlarged size to better depict structural features of the catheter;

FIG. 3B is a fragmentary view showing component parts of the catheter seen in FIG. 3A in alternative operative positions; and FIG. 4 provides a fragmentary cross sectional view similar to FIG. 3A, but depicting an alternative embodiment of the present inventive catheter.

DETAILED DESCRIPTION OF THE PREFERRED EXEMPLARY EMBODIMENTS

Referring more particularly to the drawings in which features which are analogous in structure or function so as to be similar elements of particular embodiments of the invention are indicated by identical reference numerals, FIG. 1 shows a low-profile, single-lumen perfusion balloon catheter, generally referenced with the numeral 10. In order to better illustrate the structure, as well as the functional cooperation of the structures of the catheter 10, the foreground portion of FIG. 1 is shown at a larger scale than is the background portion of this Figure.

In overview, the catheter 10 includes an elongate guide wire assembly, generally indicated with the numeral 12, and extending from end to end through the remainder of the catheter assembly. This guide wire assembly 12 is rotational and relatively movable axially of the remainder of the catheter 10, as will be further explained. A proximal end portion 14 of the guide wire assembly 12 is seen in the background portion of FIG. 1 projecting from a proximal end 16 of the remainder of the catheter 10. In the foreground portion of FIG. 1, a distal end portion 18 of the guide wire assembly 12 is also seen projecting distally from a distal end 20 of the remainder of the catheter 10. This guide wire assembly 12 includes a proximal elongate wire-like shaft portion 22, which defines the proximal end portion 14, and on which a chuck device, or "torquer", 24 is removably secured in order to allow a physician better control of the guide wire assembly 12 in order to both twist this guide wire assembly as well as to move it axially relative to the remainder of the catheter 10, if desired. This torquing and axial movement of the guide wire assembly 12 is employed in order to rotate and axially advance and retract the distal end portion 18 of the guide wire assembly to assist in steering the catheter 10 at its distal end 20 through a vascular pathway.

The guide wire shaft portion 18 extends at a constant diameter distally to a tapering portion 26, which is best seen viewing FIGS. 1 and 3A in conjunction. The tapering portion 26 leads distally to a valving portion 28 of the guide wire assembly, which will be further explained. Distally of the valving portion 28, the shaft 18 of guide wire assembly 12 joins at a weld 30 with a flexible spring-like distal end portion 32. This flexible spring-like portion 32 includes a rounded tip part 34 (seen in FIG. 1). The spring-like portion 32 may be made of or include a feature thereof which is made of radiopaque material so as to provide a marker visible with a fluoroscope for visualization of the distal end of guide wire assembly 12 by a physician.

Over the guide wire assembly 12 is received a single-lumen treatment catheter assembly 36 which defines the ends 16 and 20. This treatment catheter assembly 36 includes an elongate single-lumen shaft portion 38 having a side wall 40 defining a single through passage or lumen 42. At the proximal end 16, the treatment catheter assembly 36 includes a Y-connector 44. This Y-connector 44 is provided with a branch inflation port 46 which at a luer fitting 47 may receive pressurized fluid into the passage 42 of the treatment catheter assembly 36. The Y-connector 44 is also provided with a compression sealing hub 48 which prevents loss of the pressurized inflation fluid about the guide wire assembly 12. When the compression hub 48 is loosened by use of a finger nut 50, the guide wire assembly 12 is freely movable axially and in rotation relative to the treatment catheter assembly 36. This compression hub 48 defines the proximal end 16 for the catheter 10. The treatment catheter assembly 36 may also include a reinforcing sleeve member 52 strengthening the junction between shaft 38 and Y-connector 44.

A distal end portion 54 of the treatment catheter assembly 36 includes a number of elements which are sequentially arranged axially along the length of the catheter 10 in this end portion 54. First, adjacent to the remainder of the shaft 38, and joined thereto at a bond 56 is an expandable dilatation balloon 58 (shown deflated in FIG. 1). Next to the dilatation balloon 58 and integrally formed therewith is a cylindrical seal section 60 leading to the distal end 20 and defining a distal opening 62. The balloon 58 is seen to include a side wall 64 which is folded and over wrapped on itself to provide a comparatively small overall diameter.

As is shown in FIG. 3A, dilatation balloon 58 is formed as an integral part of the shaft 38 of treatment catheter 36, and is in fluid communication With the single axial lumen running throughout the length of tubular shaft 38 and defined by the passage 42 of this shaft. The guide wire assembly 12, as mentioned above, extends throughout the length of treatment catheter assembly 36, and beyond distal end opening 62. Distal opening 62 is provided with seal means in the form of sleeve-like seal section 60. This seal section 60 includes a non-expandable but resilient side wall portion 66 defining an inner surface 68 which is sealingly and releasably engaged by guide wire assembly 12 at the valving portion 28 thereof.

Viewing FIG. 3A, it will be seen that in the exemplary embodiment of the present invention the means of valving portion 28 of guide wire assembly 12 which releasably engages the sleeve-like section 60 in sealing relationship is formed as a sleeve-like cylindrical collar 70 which is dimensioned to slidingly and sealingly engage into the sleeve-like seal section 60 with a light friction fit. That is, the collar 70 will pass through the seal section 60 in response to either a sufficient pulling or pushing force on guide wire assembly 12, but the collar 70 does not simply fall or slip through the seal section 60.

This cylindrical collar 70 is sealingly and relatively rotatably coupled to guide wire 12, but is constrained from relative axial movement on the guide wire assembly 12 by a pair of retaining rings 72 and 74 respectively carried immovably on the guide wire assembly 12 proximally and distally of the collar 70. The retaining rings 72 and 74 may be welded or swaged onto the guide wire assembly 12, for example.

The sealing relationship of the collar 70 on the guide wire assembly 12 is established by the sealingly close fit of a cylindrical bore 76 through the collar member 70 on a cylindrical surface portion 78 of the guide wire assembly 12. Because the collar member 70 is relatively long in relation to the diameter of the bore 76, and the fit between the bore 76 and surface 78 is close, fluid leakage axially through bore 76 is minimal. However, the fit of collar member 70 on surface portion 78 of the guide wire assembly 12 is such that the latter is substantially freely rotatable relative to the collar member.

This exemplary construction produces a releasably engaging seal which fixes guide wire assembly 12 removably in position relative to balloon 58, yet which allows guide wire 12 to be rotated or "torqued" freely without wrapping balloon 58 about the shaft 38 or guide wire 12. Additionally, while the retaining collars 72, 74 are shown in FIG. 3 as being disposed immediately on each side of the collar 70, those ordinarily skilled in the pertinent arts will recognize that these collars 72 and 74, may be spaced somewhat from the collar 70 so that an added degree of sliding axial movement for the guide wire assembly 12 is provided without dislodging the sleeve-like collar 70 from sealing relation with the seal section 60.

This added degree of axial movement allows the physician to extend or retract the distal end portion 18 of guide wire assembly 12 relative to the distal end portion 54 of the treatment catheter assembly 36 and shaft 38 thereof when necessary for steering and positioning of the catheter while still retaining the seal between collar 70 and seal section 60. As will be seen the collar 70 can be disengaged when desired from the seal section 60 by axial movement of the guide wire assembly 12.

In FIG. 3A, the dashed lines depict balloon 58 inflated by a radiologically opaque or partially opaque contrast fluid. The radiopaque fluid allows the attending physician to place the balloon where desired with respect to an arterial lesion or stenosis. Also, as the dilatation balloon inflates, this enlargement in diameter of the balloon is visible to the physician who can thereby judge the extent to which the vessel is being enlarged. In the position of guide wire assembly 12 depicted in FIG. 3A, the orifice 62 is sealingly closed by the collar member 70 in seal section 60. Consequently, the balloon 58 is inflated by the contrast fluid supplied thereto via the luer fitting 47 of connector 44, and passage 42. By way of example only, the initial or deflated diameter of balloon 58 may be on the order of about 0.5 mm, and its inflated diameter may be from about 1.5 mm. Thus, the balloon 58 may provide a ratio of diameter increase from its deflated diameter to its inflated condition which in about 3:1, or more.

In order to allow perfusion blood flow past the inflated balloon 58, the catheter 36 also includes a flexible tubular perfusion conduit portion 80. This perfusion conduit 80 includes a side wall 82, which at axially spaced apart locations 84 and 86 is bonded to the shaft portion 38 of catheter 36 proximate to the bond 56, and to the seal section 60. The perfusion conduit portion 80 defines a bore 83 and respective proximal and distal axially-extending openings, 88 and 90, respectively, as well as proximal and distal perfusion ports, 92 and 94, respectively, opening from the bore 83 through the side wall 82. Intermediate of the perfusion ports 92 and 94, the perfusion conduit portion 80 includes a section, referenced with the numeral 96, which traverses the balloon 58.

In order to prevent the inflation pressure of the balloon when inflated, from collapsing the perfusion conduit portion 80 and preventing perfusion blood flow, the section 96 includes a metallic open-coil support member 98. That is, the support member 98 is configured like an open-coil spring to thereby preserve the flexibility of the distal portion 54 of the catheter 36. On the other hand, the open-coil support member 98 is effective to support the side wall 82 of the perfusion conduit member 80 in opposition to the inflation pressure effective within the balloon 58. As those ordinarily skilled in the pertinent arts will appreciate, these inflation pressures may be from 6 to 10 atmospheres, for example. However, the support member 98 is configured of wire 100 as an open-coil helix defining a bore 102, best seen in FIG. 3A. The bore 102 is coaxial with the bore 83 of the perfusion conduit portion 80. Alternatively, the coil member 98 could be made in the form of a flexible mesh tube sufficient to provide support to the conduit 80.

In order to retain the support member 98 in the bore 83 of the conduit portion 80, the support member 98 is inserted into a length of tubing which is to become the conduit portion 80. While this tubing is heated sufficiently to soften but not melt the polymeric material from which the tubing is made, an outer tubular "heat shrink" member is contracted about the tubing and support member 98. This outer contraction causes the conduit 80 to be shrunk onto the support member 98 so that the coils of wire 100 are partially embedded into the side wall 82. This embedding of the support member 98 into the polymeric material of conduit 80 securely retains the support member. Alternatively, the support member 98 could be completely embedded into the side wall 82 of the conduit 80.

FIG. 3B fragmentarily depicts the operative condition of the catheter 10 after the inflation fluid has been withdrawn to deflate the balloon 58, and the guide wire assembly 12 has been advanced axially to disengage the seal section 60 from the sealing collar 70. The remaining contrast or balloon inflation fluid may be flushed from the catheter 10, to be replaced with a treatment or drug fluid, flowing from the open end orifice 62. The catheter 10 may be retracted slightly so that the flow of treatment fluid from the open bore 76 is most concentrated at the location of the lesion just dilated with the balloon 58.

FIG. 4 depicts an alternative embodiment of the present inventive catheter which is particularly configured for use in a mono-rail mode of therapeutic treatment. After consideration of the embodiment depicted in FIG. 4, it will be apparent that the embodiment of FIGS. 1–3 may also optionally be used in a mono-rail mode of treatment if desired to facilitate catheter exchange. Considering the embodiment of FIG. 4, features analogous in structure or function to those depicted and described with reference to FIGS. 1–3 are referenced with the same numeral used above, and having a prime added thereto.

The catheter 10' includes a treatment catheter assembly 36' with a shaft 38' having a single lumen 42'. At a distal end portion 54' of the catheter shaft assembly 36', the catheter 10' includes a balloon 58', which at 104 includes a closed distal end. Similarly to the embodiment of FIGS. 1–3, the embodiment of FIG. 4 includes a perfusion conduit 80', which also serves to slidingly pass along a guide wire 106 in mono-rail configuration. The end 104 is closed by bonding a distal end portion 108 of the balloon 58' to a fixed stiffening wire 110 extending through the shaft 38'. The stiffening wire 110 provides for steering and pushing of the catheter 10' while preventing axial collapse of the balloon section 58' under such pushing. In the case of the catheter of FIG. 4, the guide wire 106 is referred to hereinafter as a "mono-rail" guide wire. It will be understood that the mono-rail guide wire 106 does not include the valving features 70–78 of the guide wire 12 of the embodiment of FIGS. 1–3. The mono-rail guide wire 106 may be a conventional wire-shaft guide wire with flexible distal end portion, which is well known in the pertinent arts.

Moreover, the perfusion conduit 80' is bonded to the catheter shaft 38' at a proximal bond 84' and at a distal bond 86' which engages the closed distal end portion 104 of the balloon 58'. As with the embodiment of FIGS. 1–3, when the balloon 58' is inflated, the perfusion conduit 80' provides for flow of perfusion blood past this inflated balloon. The bore of the perfusion conduit 80' is made large enough that the presence of the mono-rail guide wire 106 in this bore does not prevent sufficient perfusion blood from flowing through the conduit 80' past the inflated balloon 58'.

Those ordinarily skilled in the pertinent arts will recognize that the mono-rail embodiment of FIG. 4 allows the treatment catheter 36' to be withdrawn along the vascular pathway while leaving the mono-rail guide wire 106 in place. Subsequently, a replacement catheter, possibly of a larger size (not shown), may retrace the path back to the lesion under treatment along the mono-rail guide wire 106. Thus, it will be apparent that both embodiments of the present inventive catheter may be used in a mono-rail configuration. That is, when the embodiment of FIGS. 1–3 is used, if a physician anticipates the need to replace the balloon 58 with one of a larger size, a second mono-rail guide wire 106 may be advanced along the vascular pathway along with the catheter 10 as shown in FIGS. 1–3. After the first treatment catheter assembly 36 is employed to dilate and possibly to deliver therapeutic fluid to a lesion, the catheter assembly 36 is withdrawn along with its guide wire 12, leaving the mono-rail guide wire 106 still in place. Thus, a second or successive treatment catheter may retrace the path back the lesion under treatment along the mono-rail guide wire 106.

Exemplary non-limiting diameters for the proximal portion of guide wire 12 range from 0.005 to 0.016 inches whereas the preferred exemplary outer diameter for the cylindrical collar 70 ranges from approximately 0.012 to 0.020 inches. Thus, in the embodiments of the present invention illustrated the drawing Figs., the distal end portion of guide wire assembly 12 is provided with a cross-sectional diameter on the order of approximately 0.005 inches and cylindrical collar 70 is formed of a polymeric material such as polytetrafluoroethylene (PTFE) having an outer diameter of approximately 0.016 inches and a wall thickness of approximately 0.005 inches.

It should be emphasized that the diameter of guide wire assembly 12 need not be constant and may taper in the distal end portion to provide an enhanced degree of flexibility toward the distal end of the guide wire assembly. Guide wire assembly 12 itself is preferably formed of metal such as stainless steel but also may be constructed of polymers or polymer coated metals as is known in the art. An exemplary overall wire length for guide wire assembly 12 is on the order of 175 cm.

Although not essential to the practice of the present invention, guide wire assembly 12 is preferably provided at flexible distal spring coil 32 with a radiopaque portion in order to provide visualization as guide wire assembly 12 is advanced along a vascular pathway. Spring coil 32 may be formed of any resilient material, preferably metal, and in the preferred embodiment of the present invention is formed of a radiopaque material such as platinum, gold, or tantalum. Thus, spring coil 32 with tip 34 functions as an additional marker to assist the physician in positioning the apparatus of the present invention.

Though spring coil 32 is illustrated in the drawing Figs. as being relatively straight, it is commonly known in the art to pre-curve spring coil 32 so that the implanting physician can rotate wire assembly 12 and direct tip 34 of wire coil 32 into specific vascular junctions to direct the entire assembly along the proper pathway. Rotational manipulation of wire 12, or "torquing" as it is referred to in the art, is accomplished by rotating the proximal end portion 14 of the guide wire assembly. As is well known in the art, this rotation may be achieved with use of a variety of clamps or chuck devices like the torquer 24 which provide the physician with purchase on the wire 12. The axially flexible construction of guide wire 12 transmits this torque along the entire longitudinal extent of wire 12 to coil 32. However, because cylindrical collar 70 is preferably sealingly coupled to guide wire 12 in a relatively rotatable manner, this torque is not transmitted to balloon 58, and prevents this balloon from wrapping in a spiral fashion around guide wire 12.

Flexible tubular shaft 38 is preferably formed of a polymeric material such as polyethylene, polyamide, polyimide, polypropylene, polyvinyl, polyester such as polyethyleneterephthalate (PET), or polyolefin copolymer. Additionally, to improve its lubricity, shaft 38 may be coated with PTFE, silicone or other materials including low friction lubricants. Similarly, low friction coatings such as polyamide or fluoropolymer or such as PTFE or hydrophilic materials and lubricants may be utilized to enhance the movement of all components of catheter 10 during angioplasty. Resilient sleeve-like seal section 60 may be formed from the same material forming the remainder of tubular shaft 38, or it may alternatively be formed from a lubricous polymeric material. Alternatively, resilient sleeve 60 may be coated along its inner surface with a lubricous material to facilitate its engagement with cylindrical collar 70.

Cylindrical collar 70 similarly can be formed of a wide variety of materials ranging from stainless steel to polymeric materials and may even be formed as an integral part of guide wire assembly 12. However, it is preferred that collar 70 be formed of a polymeric material such as PVC, polyamide, polyimide, or fluoropolymer such as polytetrafluoroethylene (PTFE) as this provides an added degree of flexibility to the guide wire assembly 12 within the distal end portion 20 of the catheter 10.

In closing it is to be understood that the embodiments of the invention disclosed herein are illustrative of the principals of the invention and that other modifications may be employed which are within the scope thereof. Accordingly, the present invention is not limited to that precisely as shown and described in the specification.

What is claimed:

1. A perfusion balloon catheter comprising a catheter shaft which at a distal end portion thereof carries an expansible balloon section, a perfusion conduit exterior to the balloon section and defining proximal and distal perfusion openings respectively disposed relative to said balloon section and communicating with one another via a passage of said perfusion conduit, and a support member for supporting said perfusion conduit in opposition to inflation pressure from said balloon section and maintaining said perfusion conduit passage open to permit perfusion blood flow past said balloon while the latter is forcefully inflated with pressurized fluid.

2. The catheter of claim 1 further including an inflation lumen communicating pressurized inflation fluid to said expansible balloon section.

3. The catheter of claim 2 further including a guide wire assembly movably disposed in said inflation lumen.

4. The catheter of claim 3 wherein said guide wire assembly includes means for valvingly cooperating with said catheter to contain pressurized fluid within said expansible balloon section.

5. The catheter of claim 4 wherein said catheter includes a seal section defining a distal opening from said balloon section, said guide wire assembly valving means including a seal collar sealingly receivable in a first position in said seal section to contain said pressurized fluid within said balloon section.

6. The catheter of claim 5 wherein said seal collar including a collar member relatively rotatably carried on a shaft portion of said guide wire assembly.

7. The catheter of claim 6 wherein said collar member is formed of polymeric material.

8. The catheter of claim 7 wherein said polymeric material is selected from the group including PVC, polyamide, polyimide, and fluoropolymers such as polytetrafluoroethylene.

9. The catheter of claim 1 wherein said support member includes a helical coil member.

10. The catheter of claim 9 wherein said helical coil member includes a helical coil of metallic wire.

11. The catheter of claim 10 wherein said helical coil of metallic wire is of open-coil configuration.

12. The catheter of claim 1 further comprising said perfusion conduit defining one of a proximal and a distal perfusion port opening outwardly from said perfusion conduit passage.

13. The catheter of claim 12 wherein said perfusion conduit includes both a proximal and a distal perfusion port opening outwardly from said passage on said conduit.

14. The catheter of claim 1 further including a monorail guide wire assembly slidably received through said perfusion conduit.

15. The catheter of claim 14 wherein said balloon section is closed at a distal end thereof.

16. A method of providing perfusion blood flow past a dilatation balloon of a medical treatment catheter when said dilatation balloon is inflated to dilate a circulatory pathway, said method including the steps of:
providing a medical treatment catheter comprising an elongate catheter shaft defining an inflation lumen, said catheter shaft at a distal end portion thereof carrying an inflatable dilatation balloon in fluid communication with said inflation lumen;
providing a perfusion conduit exterior to said dilatation balloon and defining openings proximal and distal of the dilatation balloon which communicate fluidly with one another via a passage of said perfusion conduit;
providing a support member for supporting said perfusion conduit in opposition to inflation pressure in said dilatation balloon so that said passage of said perfusion conduit remains open when said dilatation balloon is forcefully inflated and allows perfusion blood to flow past said balloon; and
allowing blood through said perfusion conduit when said dilatation balloon is forcefully inflated.

17. The method of claim 16 wherein said step of providing a support member for supporting said perfusion conduit includes the steps of providing a helical coil member, and inserting said helical coil member into said passage of said perfusion conduit congruently with said dilatation balloon.

18. The method of claim 17 wherein said step of inserting said helical coil member into said passage includes the steps of constraining the opposite ends of said helical coil member, twisting said opposite ends to reduce the diameter of said helical coil member to a size less than its unconstrained diameter, inserting said constrained and twisted helical coil member into said passage, allowing said helical coil member to return toward its unconstrained diameter, and employing said return of said helical coil member toward its unconstrained diameter to cause an interference fit of said helical coil member within said passage.

19. A low-profile single-lumen balloon dilatation perfusion catheter comprising:
an elongate single-lumen catheter shaft having an inflation lumen extending there along;
a balloon section carried on said catheter shaft in a distal end portion thereof and in fluid communication with said inflation lumen;
a perfusion conduit member carried on said catheter shaft at said distal end portion thereof and exterior to said balloon section to defining proximal and distal perfusion openings communicating with one another via a passage of said perfusion conduit member; and
a support member for supporting said perfusion conduit in opposition to inflation pressure expanding said balloon section to thereby maintain said passage open for perfusion blood flow past said balloon section.

20. The perfusion catheter of claim 19 further including a guide wire assembly for guiding said catheter along a vascular pathway.

21. The perfusion catheter of claim 20 wherein said guide wire assembly is received slidably through said perfusion conduit.

22. The perfusion catheter of claim 20 wherein said guide wire assembly is received slidably in said inflation lumen, and said catheter and guide wire assembly include valving means for sealingly cooperating with one another to maintain pressurized inflation fluid in said balloon section.

23. A perfusion balloon catheter comprising:
a catheter shaft which at a distal end portion thereof carries an expansible balloon section;
an inflation lumen communicating pressurized inflation fluid to said expansible balloon section;
a guide wire assembly movably disposed in said inflation lumen;
a perfusion conduit traversing the balloon section and defining proximal and distal perfusion openings respectively disposed relative to said balloon section and communicating with one another via a passage of said perfusion conduit; and
a support member for supporting said perfusion conduit in opposition to inflation pressure from said balloon section, whereby said support member maintains said perfusion conduit passage open to permit perfusion blood flow past said balloon while the latter is forcefully inflated with pressurized fluid;
wherein said guide wire assembly includes means for valvingly cooperating with said catheter to contain pressurized fluid within said expansible balloon section.

24. The catheter of claim 23 wherein said catheter includes a seal section defining a distal opening from said balloon section, said guide wire assembly valving means including a seal collar sealingly receivable in a first position in said seal section to contain said pressurized fluid within said balloon section.

25. The catheter of claim 24 wherein said seal collar includes a collar member relatively rotatably carried on a shaft portion of said guide wire assembly.

26. The catheter of claim 25 wherein said collar member is formed of polymeric material.

27. The catheter of claim 26 wherein said polymeric material is selected from the group including PVC, polyamide, polyimide, and fluoropolymers such as polytetrafluoroethylene.

28. A low-profile single-lumen balloon dilatation perfusion catheter comprising:
an elongate single-lumen catheter shaft having an inflation lumen extending there along;
a balloon section carried on said catheter shaft in a distal end portion thereof and in fluid communication with said inflation lumen;
a perfusion conduit member carried on said catheter shaft at said distal end portion thereof and outwardly traversing said balloon section to define proximal and distal perfusion openings communicating with one another via a passage of said perfusion conduit member;
a support member for supporting said perfusion conduit in opposition to inflation pressure expanding said balloon section to thereby maintain said passage open for perfusion blood flow past said balloon section; and
a guide wire assembly received slidably through said perfusion conduit for guiding said catheter along a vascular pathway;
wherein said catheter and guide wire assembly include valving means for sealingly cooperating with one another to maintain pressurized inflation fluid in said balloon section.

* * * * *